United States Patent [19]

Jung et al.

[11] Patent Number: 5,426,206

[45] Date of Patent: Jun. 20, 1995

[54] STEREOSPECIFIC SYNTHESIS OF ALDOLS

[75] Inventors: Michael E. Jung, Los Angeles; Derin C. D'Amico, Santa Monica, both of Calif.

[73] Assignee: The Regents of the University of California, Oakland, Calif.

[21] Appl. No.: 157,477

[22] Filed: Nov. 24, 1993

[51] Int. Cl.$^6$ .......................... C07F 7/08; C07F 7/18
[52] U.S. Cl. ......................... 556/436; 568/309; 568/322; 568/403; 568/405; 568/406; 568/811; 568/853
[58] Field of Search ................ 556/436; 568/811, 853, 568/309, 322, 403, 405, 406

[56] References Cited

U.S. PATENT DOCUMENTS

| | | | |
|---|---|---|---|
| 5,037,855 | 8/1991 | Sato | 556/436 X |
| 5,329,023 | 7/1994 | Brussee et al. | 556/436 X |

OTHER PUBLICATIONS

S. Masamune et al., *Aldrichimica Acta, Advances in Stereochemical Control: The 1,2-and 1,3-Diol Systems*[1], Aldrich Chemical Co., vol. 15, No. 3, (1982), pp. 47-68.

A. Togni et al., *Cooperativity of Chirality in Homogeneous Catalysis: The Gold(I)-Catalyzed Aldol Reaction and the Vanadium(IV)-Catalyzed Hetero Diels-Alder Cycloaddition*, Chirality, vol. 3, No. 4, (1991) pp. 331-340.

Manfred Braun, *Recent Developments in Stereoselective Aldol Reactions*, Advances in Carbanion Chemistry, JAI Press, Inc., vol. 1, (1992) pp. 177-247.

Heathcock, C. H. "The Aldol Addition Reaction," in *Asymmetric Synthesis;* Morrison, J. D., Ed.; Academic Press: New York 1984; vol. 3, Ch. 2 pp. 111-115.

Evans, D. A.; Nelson, J. V.; Taber, T. R. *Top. Stereochem* 1982, 13, 1-6.

Paterson, I.; Lister, M. A.; McClure, C. K. *Tetrahedron Lett* 1986, 27, 4787-4790.

Reetz, M. T.; Kunisch, F.; Heitman, P. *Tetrahedron Lett.* 1986, 27, 4721-2724.

Maruoka, K.; Sato, J.; Yamamoto, H. *Tetrahedron* 1992, 48, 3749-3762.

Maruoka, K.; Ooi, T.; Yamamoto, H., *J. Am. Chem. Soc.* 1989, 111 6431-6998.

Maruoka, K.; Ooi, T.; Nagahara, S.; Yamamoto, H. *Tetrahedron* 1991, 47, 6983-6998.

Maruoka, K.; Hagesawa, M.; Yamamoto, H.; Suzuki, K.; Shimazaki, M.; Tsuchihashi, G. *J. Am Chem. Soc.* 1986, 108, 3827-3829.

Suzuki, K.; Miyazawa, M.; Tsuchihashi, G. *Tetrahedron Lett.* 1987, 28, 3515-3518.

Shimazaki, M.; Hara, H.; Suzuki, K.; Tsuchiahashi, G. *Tetrahedron Lett.* 1987, 28, 5891-5894.

Still, W. C.; Gennari, C. *Tetrahedron Lett* 1983 24, 4405-4408.

Hoveyda, A. H.; Evans, D. A.; Fu, G. C. *Chem Rev.*, 1993, 93, 1307-1370.

Hanson, R. M.; Sharpless, K. B., *J. Org. Chem* 1986, 51, 1922-1525.

Olah, G. A.; Farooq, I.; Farnia, S. M. F.; Olah, J. A., *J. Am Chem Soc.* 1988, 110, 2560-2565.

Alexakis, A.; Mutti, S.; Normant, J. F.; Mangency, P. *Tetrahedron Asymm.* 1990, 1, 437-440.

Basavaiah, D.; Sarma, P. K. S. *J Chem Soc., Chem. Commun* 1992, 955-557.

Sreekumar, C.; Darst, K. P.; Still, W. S. *J. Org. Chem* 1980, 45, 4260-4262.

Davis, A. P.; Jaspars, M. *Angew. Chem. Int. Ed. Engl.,* 1992, 31, 470-471.

*Primary Examiner*—Paul F. Shaver
*Attorney, Agent, or Firm*—Christie, Parker & Hale

[57] ABSTRACT

Methods are provided for preparing all four diastereomers of 2-alkyl-3-hydroxyalkanals, 2-alkyl-3-silyloxyalkanals, and the like, with high enantiocontrol, using non-aldol chemistry. The synthetic methods also provide novel, stereospecific routes to polypropinates and chiral 2-substituted-1,3 diols.

19 Claims, No Drawings

STEREOSPECIFIC SYNTHESIS OF ALDOLS

ACKNOWLEDGEMENT OF GOVERNMENT SUPPORT

This invention was made with government support under Grant No. GM 31349 awarded by the National Institutes of Health. The government has certain rights in the invention.

FIELD OF THE INVENTION

This invention is directed to processes for making aldols, including 2-substituted-3-silyloxyalkanals and 2-substituted-3-hydroxyalkanals; chiral 1,3 diols; and chiral polypropionates.

BACKGROUND OF THE INVENTION

Aldols ($\beta$-hydroxy- and $\beta$-alkoxy aldehydes) are useful chemical compounds used in the manufacture of antibiotics and other medicinal compounds, and in various natural products syntheses. The carboxylic acid analogs of certain chiral aldols have been used in liquid crystal applications.

Typically, aldols are prepared by an aldol condensation reaction. For example, the compound named "aldol" ($\beta$-hydroxybutyraldehyde) is prepared by condensation of acetaldehyde in sodium hydroxide solution. Schematically, an aldol condensation is expressed by the equation:

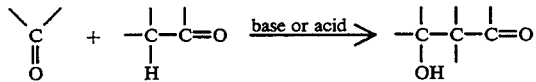

Over the years, a large amount of chemistry has been developed to produce aldol products with high diastereomeric and enantiomeric control. The following reviews are illustrative: Heathcock, C. H. "The Aldol Addition Reaction," in *Asymmetric Synthesis*; Morrison, J. D., Ed.; Academic Press: New York, 1984; Vol. 3, Ch.2, pp 111–212; Braun, M. "Recent Developments in Stereoselective Aldol Reactions," in *Advances in Carbanion Chemistry*, Snieckus, V., Ed.; Jai Press: Greenwich, Conn., 1992; Vol. 1, Ch. 4; Togni, A.; Pastor, S. D. *Chirality* 1991, 3,331; Evans, D. A.; Nelson, J. V.; Taber, T. R. Top. *Stereochem.* 1982, 13,1; and Masamune, S.; Choy, W. *Aldrichim. Acta* 1982, 15,47. For some recent specific examples, see: Paterson, I.; Lister, M. A.; McClure, C. K. *Tetrahedron Lett.* 1986, 27,4787 and references therein; and Reetz, M. T.; Kunisch, F.; Heitman, P. *Tetrahedron Lett.* 1986,27,4721.

In general, the known methods for enantiocontrol utilize an aldol reaction with well-designed chiral auxiliaries to produce the desired enantiomers with, at times, quite high selectivity. A few exceptions to this generalization are known, however. In a series of papers, Yamamoto has shown that hindered aluminum-based Lewis acids can promote rearrangements of epoxy silyl ethers to produce various products, including both erythro and threo aldols. See Maruoka, K.; Sato, J.; Yamamoto, H. *Tetrahedron* 1992, 48, 3749; Maruoka, K.; Ooi, T.; Yamamoto, H. *J. Am. Chem. Soc.* 1989, 111, 6431; and Maruoka, K.; Ooi, T.; Nagahara S.; Yamamoto, H. *Tetrahedron* 1991, 47, 6983. In each case, however, the group being transferred is originally attached to the epoxide carbon, and not to the adjacent carbon (the carbon that becomes the $C_2$ position, $\alpha$ to the aldehyde).

Tsuchihashi has observed transfer of alkyl groups from adjacent carbons to tertiary epoxide centers to generate quaternary carbons $\alpha$ to ketones, but has not reported the preparation of tertiary centers or aldehydes by that approach. See Maruoka, K.: Hagesawa, M.; Yamamoto, H.; Suzuki, K.; Shimazaki, M.; Tsuchihashi, G. *J. Am. Chem. Soc.* 1986, 108, 3827; Suzuki, K.; Miyazawa, M.; Tsuchihashi, G. *Tetrahedron Lett.* 1987, 28 3515; and Shimazaki, M.; Hara, H.; Suzuki, K.; Tsuchihashi, G. *Tetrahedron Lett.* 1987, 28, 5891.

In a joint paper, Tsuchihashi and Yamamoto reported the migration of phenyl and vinyl groups in the presence of $TiCl_4$ and $Et_3SiH$ to produce primary alcohols. See *J.Am. Chem. Soc.* 1986, 108, 3827.

Despite the success of such methods, however, the preparation of particular aldols having specific stereoconfigurations at the $C_2$ and $C_3$ positions can be problematic. Thus, new, stereoselective routes to aldols, particularly 2-alkyl-3-silyloxyalkanals and 2-alkyl-3-hydroxyalkanals, are desired.

SUMMARY OF THE INVENTION

It has now been discovered that all four diastereomers of the aldol products, 2-substituted-3-silyloxyalkanals and 2-substituted-3-hydroxyalkanals can be prepared with high enantiocontrol by a unique non-aldol route. The absolute stereoconfiguration at the $C_2$ and $C_3$ positions is introduced by preparing an epoxyalcohol by an asymmetric epoxidation reaction. Treatment of the epoxyalcohol with a silyl reagent, such as a trialkylsilyl triflate, opens the epoxide regioselectively with inversion of configuration to form the silyloxyalkanal. Removal of the silyloxy group and replacement with OH gives the 2-substituted-3-hydroxyalkanal.

The method is sufficiently general in scope to allow the synthesis of optically active 2-alkyl- and 2-aryl-3-silyloxyalkanals, and the analogous 2-substituted-3-hydroxyalkanals, and also provides a novel stereospecific route to polypropionates and chiral 2-substituted-1,3-diols, using non-aldol chemistry.

In an exemplary embodiment of the invention, all four diastereomers of 2-methyl-3-(t-butyldimethyl-silyloxy)hexanal are prepared in excellent yield from the simple aldehyde, butanal, by the following steps: (a) conversion of the aldehyde to the allylic alcohol, 2-methylhex-2enol; (b) formation of an epoxyalcohol by Sharpless epoxidation of the allylic alcohol; and (c) treatment of the epoxyalcohol with t-butyldimethylsilyl triflate to form 2-methyl-3-(t-butyldimethyl-silyloxy)-hexanal.

In another embodiment of the invention, the chiral diol 2-methylhexan-1,3-diol is prepared with high diastereomeric and enantiocontrol by reducing the aldehyde functionality on a 2-methyl-3-silyloxyalkanal, removing the 3-silyloxy group, and replacing it with OH, using a deprotecting agent.

In still another embodiment of the invention, the polypropionate (2S,3S,4S,5R)-5-(triethylsilyloxy)-3-hydroxy-2,4-dimethyloctanal is made from a silyloxy epoxyalcohol that is prepared using the non-aldol chemistry described herein.

DETAILED DESCRIPTION

The present invention provides a new route to optically active 2-alkyl-3-silyloxyalkanals, 2-alkyl-3-hydroxyalkanals, and 2-aryl- analogs thereof, using non-aldol chemistry, i.e., without the step of an aldol condensation. Thus, the present invention provides a unique synthetic route to optically active compounds of the formula (I):

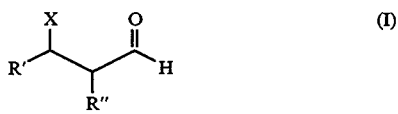

where R' and R'' are alkyl or aryl, and X is a silyloxy group, preferably a trialkylsilyloxy group, such as t-butyldimethyl-silyloxy, triethysilyloxy, triisopropyl-silyloxy, trimethylsilyloxy, etc.

The silyloxy group, X, can be easily removed and replaced with a hydroxyl group, OH, by, e.g., treatment with a deprotecting agent such as hydrogen fluoride-pyridine complex, tetrabutylammonium fluoride, etc. Thus, the present invention also encompasses a new synthetic route to optically active compounds of the formula (Ia):

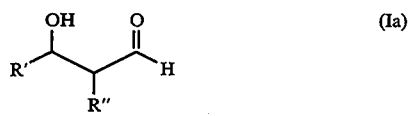

where R' and R'' are as defined above.

Technically, the Si—O, rather than the O—C, bond is broken during deprotection, or else inversion of configuration at the carbon center would be observed. Thus, deprotection actually entails removal of the silyl group and replacement with H. For ease of discussion, however, and as used herein, the step of deprotecting a protected hydroxy group shall be referred to as "removing the silyloxy group and replacing it with OH," or similar language.

The synthetic methods of this invention allow the enantiospecific synthesis of all four diastereomers of compounds of both formulas (I) and (Ia). Stereochemistry at the $C_2$ and $C_3$ positions is controlled through an asymmetric epoxidation of an allylic alcohol to yield an epoxyalcohol having a predetermined absolute stereoconfiguration. Such an epoxyalcohol is represented by the formula (II):

Treatment of the epoxyalcohol with a silyl reagent such as a trialkylsilyl triflate opens the epoxide regiospecifically with inversion of configuration to generate the desired 2-alkyl- or 2-aryl-3-silyloxyalkanal.

Alternatively, the epoxyalcohol is first reacted with a silyl reagent such as a trialkylsilyl halide, to form an epoxy silyl ether of the formula (III):

where X is a silyloxy group. Treatment with a Lewis acid, such as $BF_3$ etherate yields the desired alkanal.

As a first exemplary embodiment of the invention, the enantiospecific synthesis of all four diastereomers of 2-methyl-3-(t-butyldimethylsilyloxy)-hexanal will now be described. In this and the following descriptions and examples, particular reactants, intermediates, and products are identified by bold Arabic numbers, as needed for clarity. Complete reaction conditions (concentrations and amounts of reactants and reagents; temperatures; etc.) are provided in the examples at the end of the specification.

(2S,3R)-2-methyl-3-(t-butyldimethylsilyloxy) hexanal 5

This compound is prepared by first converting the simple aldehyde butanal 1 into E-2-methylhex-2-enol 2 by a Wittig reaction with the phosphonate $CH_3CH(COOCH_3)PO(OCH_3)$ and reduction with diisobutylaluminum hydride (DIBAL):

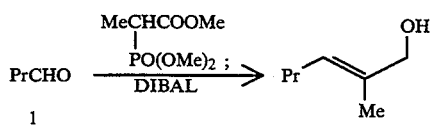

where Pr is propyl and Me is methyl. (Large quantities of allylic alcohols such as 2 are better prepared using a modified Bayliss-Hillman procedure, as described in Example 1 at the end of the specification.)

The allylic alcohol 2 is converted into the optically active epoxyalcohol (2R,3R)-2-methyl-3-propyloxiranemethanol 3, in 94% yield and 95% enantiomeric excess ("ee"), by a Sharpless asymmetric epoxidation reaction, using D-(−)-diisopropyl tartrate as the chiral catalyst:

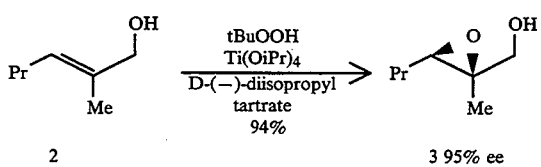

The desired alkanal is formed by treating the epoxyalcohol 3 with t-butyldimethylsilyl triflate ("TBSOTf") at low temperature:

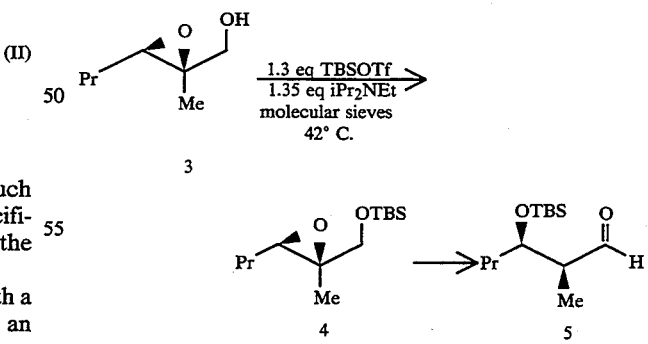

Although not bound by theory, it is believed that the mechanism of this novel transformation involves activation of the epoxide oxygen with the silyl triflate, followed by intramolecular hydride transfer to generate the new stereochemical center at the $C_2$ position and loss of the trialkylsilyl group to give the syn aldol product 5. Such a mechanism may be illustrated by the following equation:

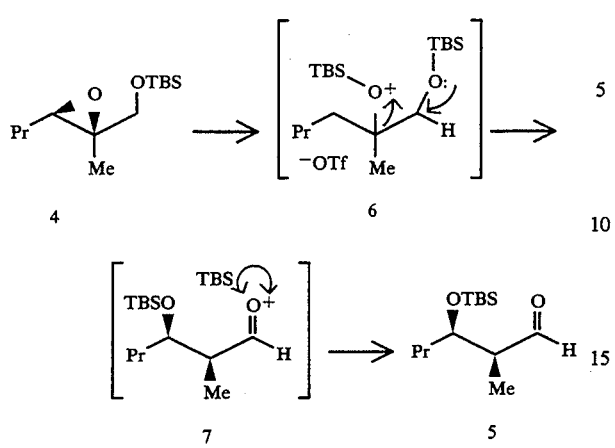

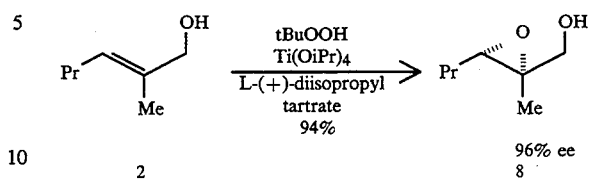

In practice, treating the epoxyalcohol 3 with one equivalent of the silyl triflate yields approximately an 88:12 mixture of the silyl ether 4 and the rearrangement product—the silyloxyalkanal 5. If an excess of silyl triflate is used, the reaction is driven essentially all the way to the silyloxyalkanal 5. However, the reaction appears to be somewhat dependent on the concentration of epoxyalcohol. For example, treating a 0.1 molar epoxyalcohol—dichloromethane solution with 1 to about 1.4 equivalents of silyl triflate yields a mixture of the silyl ether 4 and the silyloxyalkanal 5. If the concentration of epoxyalcohol is increased to about 0.3 molar or higher, however, treatment with even 1.2 equivalents of silyl triflate drives the reaction all the way to the silyloxyalkanal 5.

In an alternate embodiment, the silyl ether 4 is preformed by reacting the epoxyalcohol with the silyl reagent t-butyldimethylsilyl chloride ("TBSCl"), in the presence of Hunig's base (diisopropylethylamine) and dichloromethane (1.3 eq TBSCl, 5 eq Hunig's base, 12 h, heat; >90%). The silyl ether 4 is then treated with a Lewis acid, such as $BF_3$ etherate, which opens the epoxide regioselectively and generates the 2-methyl-3-trialkylsilyloxyalkanal 5. The yield is only slightly lower than for the one-step process.

Though not bound by theory, it is believed that this alternate route proceeds by a mechanism where the $BF_3$ complexes with the epoxide, and internal hydride transfer occurs as with the silyl triflate to give the analog of 7, which then internally transfers the silyl group from the oxonium salt to the $ROBF_3$ group (with loss of $BF_3$) to give the observed product 5.

Despite the utility of this latter approach, which is less expensive because it employs $BF_3$, rather then a silyl triflate, the best conditions are direct treatment of the epoxyalcohol 3 with 1.3 equivalents of TBSOTf and 1.35 equivalents of Hunig's base, in the presence of molecular sieves, at −42° C. to give the desired product 5 in 87% crude yield. Both capillary GC and NMR analysis show this compound to be a greater than 50:1 mixture at the center α to the aldehyde (the $C_2$ position). After purification by chromatography (during which, some epimerization occurs at the $C_2$ position), a 96:4 mixture is isolated in 78% yield.

(2R,3S)-2-methyl-3-(t-butyldimethylsilyloxy)hexanal 9

The enantiomer of 5 is prepared in like manner. The allylic alcohol E-2-methylhex-2-enol 2 is converted into the optically active epoxyalcohol (2S,3S)-2-methyl-3-propyloxiranemethanol 8 (the enantiomer of 3) in 94% yield and 96% enantiomeric excess by Sharpless epoxidation, using the L-(+)-diisopropyl tartrate as the chiral catalyst:

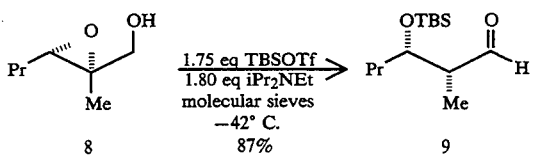

Rearrangement using TBSOTf as before yields the desired syn aldol product 9, as a greater than 99:1 mixture at the $C_2$ position. After chromatography, a 92:8 mixture is isolated in 87% yield:

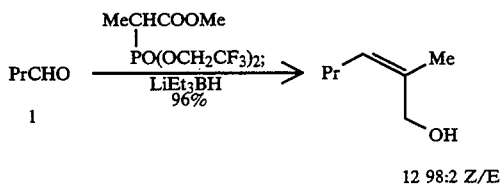

The anti aldol products 14 and 16 are prepared in a similar manner, beginning with a Z-allylic alcohol.

(2S,3S)-2-methyl-3-(t-butyldimethylsilyloxy)hexanal 14

Butanal 1 is treated with the bis(trifluoroethoxy) phosphonate reagent of Still* to give the Z-α,β-unsaturated ester, which is not isolated but directly reduced with Super Hydride ($LiEt_3BH$) in a one pot mixture to give the Z-allylic alcohol (Z)-2-methyl-2-hexen-1-ol 12 in 96% yield as the major component of a 98:2 Z/E mixture:

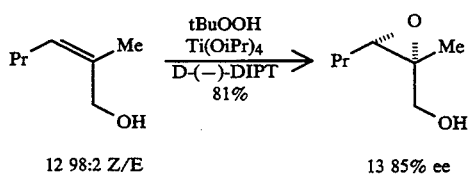

Sharpless epoxidation of the allylic alcohol 12 with the chiral catalyst D-(−)diisopropyl tartrate gives the desired epoxyalcohol (2R,3S)-2-methyl-3-propyloxiranemethanol 13 in 81% yield and 85% enantiomeric excess:

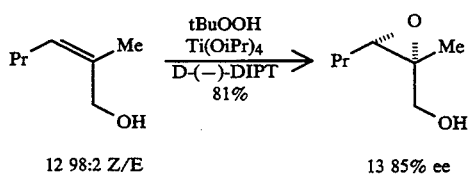

* Still, W. C.; Gennari, C. *Tetrahedron Lett* 1983 24, 4405.

Rearrangement of the epoxyalcohol with TBSOTf and Hunig's base gives the desired anti aldol product (2S,3S)-2-methyl-3-(t-butyldimethylsilyloxy)hexanal 14, as a greater than 50:1 crude mixture (more than 20:1 after column chromatography):

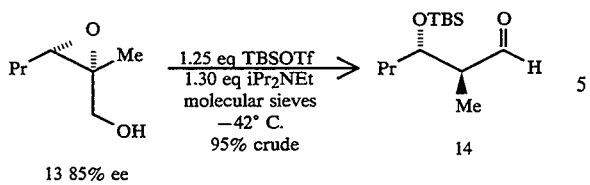

(2R,3R)-2-methyl-3-(t-butyldimethylsilyloxy)hexanal 16

The enantiomer of 14 is prepared in like manner. The allylic alcohol Z-2-methyl-2-hexen-1-ol 12 is converted into the anti aldehyde 16 via the optically active epoxyalcohol (2S,3R)-2-methyl-3-propyloxiranementhanol 15 in comparable yield and stereochemical purity, using L-(+)-diisopropyl tartrate as the chiral catalyst:

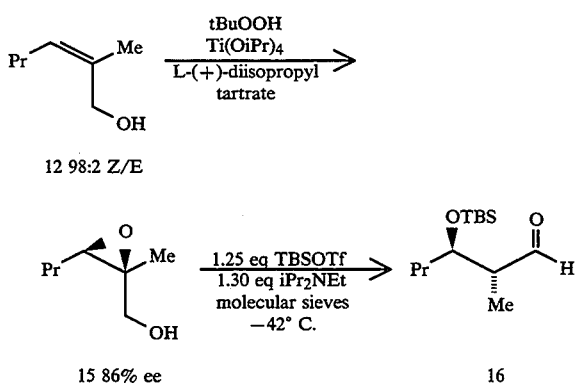

Thus, E-allylic alcohols give syn aldol products while Z-allylic alcohols give anti aldol products. Through a three-step process—Wittig and reduction; epoxidation; and rearrangement—the simple aldehyde butanal is converted into all four diastereomers of 2-methyl-3-(t-butyldimethylsilyloxy)hexanal in high yield and with excellent enantioselectivity.

The relative stereochemistry of both the syn and anti products can be confirmed by $^1$H NMR analysis of the corresponding acetonide (prepared by reduction of the aldehyde to the primary alcohol, fluoride removal of the TBS group, and acetonide formation). The coupling constants observed for the protons α to the oxygen atoms are those expected for the structures drawn.

(2S,3R)-2-methyl-3-(triethylsilyloxy)-4-phenylbutanal 11

As a second exemplary embodiment, a benzylic system is converted into a β-triethylsilyloxy aldehyde in good overall yield and enantiomeric excess.

First, the allylic alcohol E-2-methyl-4-phenylhex-2-enol is epoxidized to the epoxyalcohol (2R,3R)-2-methyl-3-phenylmethyloxiranemethanol 10 using D-(—)-diisopropyl tartrate as the chiral catalyst:

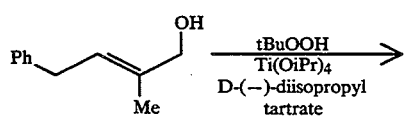

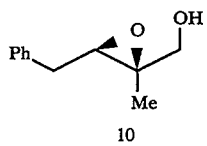

The epoxyalcohol 10 is converted into the syn aldol product 11 by reacting it with triethylsilyloxy triflate ("TESOTf") in the presence of collidine:

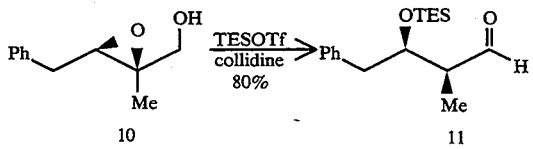

The enantiomer of 11 may be prepared using L-(+)-diisopropyl tartrate as the chiral catalyst. Similarly, the anti aldol products may be prepared by starting with the Z-allylic alcohol Z-2-methyl-4-phenylhex-2-enol.

It will be appreciated by those skilled in the art that many other aldols can be prepared by the methods described above. For example, although in each of the examples above the silyloxyalkanal is substituted at the C$_2$ position (α to the aldehyde) with a methyl group, the invention is not so limited. Rather, the synthetic schemes described herein are sufficiently general to afford routes to numerous aldols, substituted at the C$_2$ position with other alkyl and aryl groups.

Similarly, other silyl triflates can be used, including, for example, triisopropylsilyl triflate, trimethylsilyloxy triflate, etc. In short, the invention is not limited to methods for producing the silyloxy hexanals and silyloxy phenylbutanals described above, but is sufficiently broad in scope to afford the preparation of optically active compounds of the formulas (I) and (Ia), shown above.

Chiral 1,3-Diols

As another embodiment of the invention, the nonaldol synthesis of chiral silyloxyalkanals described above provides a route to chiral, optically active 1,3-diols, i.e., compounds having the formula (IV):

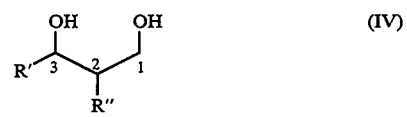

where R' and R" are alkyl or aryl. Such compounds are prepared by selecting a silyloxyalkanal having the desired stereoconfiguration at C$_2$ and C$_3$; reducing the aldehyde functionality by, e.g., treatment with NaBH$_4$ or the like; and removing the silyloxy group and replacing it with OH, using any of several known deprotecting agents, such as HF-pyridine complex, tetrabutylammonium fluoride, etc. The following two examples are representative, and in no way limiting, examples of this aspect of the invention.

(2R,3R)-2-methylhexan-1,3-diol 26

This compound is prepared by first reducing the aldehyde functionality of the syn silyloxyalkanal (2S,3R)-2-methyl-3-(triethylsilyloxy)hexanal 21 (which is identical to compound 5 above, except for the identity of the silyloxy group) using NaBH$_4$ in methanol:

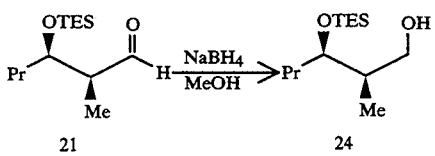

The alcohol 24 is then treated with tetrabutylammonium fluoride (on silica gel) to deprotect the hydroxy group at C₃, giving the syn 1,3-diol 26:

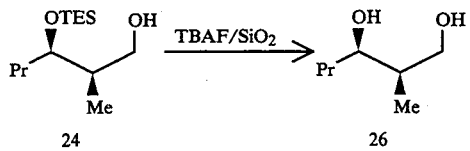

(2R,3S)-2-methylhexan-1,3-diol 27

This anti diastereomer of 26 is prepared in like manner, starting with the anti silyloxyalkanal (2S,3S)-2-methyl-3-(triethylsilyloxy)hexanal 22:

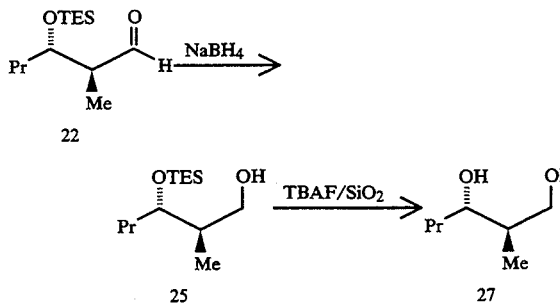

The two other diastereomers can be prepared in like manner, starting with the appropriate silyloxyalkanal. The stereochemistry of these compounds is verified by converting the diol to an acetonide, using 2,2-dimethoxypropane and p-toluenesulfonic acid. ("TsOH"), as shown for diol 26 by the following equation:

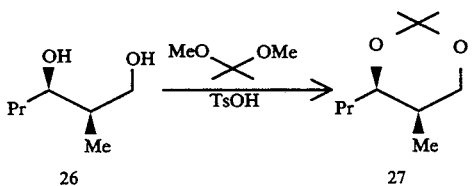

Experimental details are found at the end of the specification.

It will be readily apparent that numerous optically active 1,3-diols can be prepared in this way, form chiral silyloxyalkanals.

Polypropionates

One of the major advantages of the invention is its usefulness in the preparation of polypropionates. In particular, the regioselective opening of the epoxy silyl ether yields a product which can be viewed as a protected aldehyde, and which may be directly converted into an allylic acid, an epoxyalcohol and, ultimately a polypropionate. In contrast, in most known aldol processes, one must first protect the β-hydroxy group and convert the acyl unit into an aldehyde.

As a first exemplary embodiment of this aspect of the invention, the syn aldol product (2S,3R)-2-methyl-3-(t-butyldimethylsilyloxy)hexanal 5 is first converted into Z-allylic alcohol (4R,5R)(Z)-5-(t-butyldimethylsilyloxy)-2,4-dimethyl-2-octen-1-ol 17, in 72% yield:

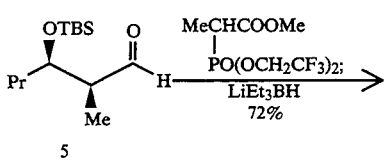

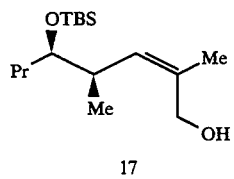

The allylic alcohol 17 is then epoxidized with the peracid meta-chloroperoxybenzoic acid (MCPBA), generating the silyloxy epoxyalcohol (2R,3S,4R,5R)-5-(t-butyldimethylsilyloxy)-2,3-epoxy-2,4-dimethyl-1-octanol 18 as the major isomer of a 12:1 stereochemical mixture:

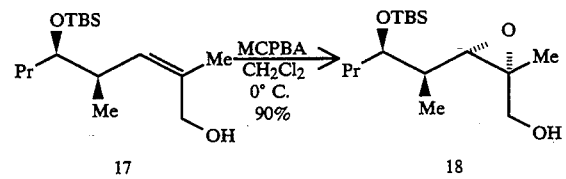

Alternatively, the epoxidation of 17 may be carried out using an external source of chirality, as in the Sharpless epoxidations described above. However, epoxidation of chiral allylic alcohols often proceeds with greater stereoselectivity when using a peracid or metal catalyst and the resident chirality present in the alkene. (For a review of such substrate-directed reactions, see Hoveyda, A. H.; Evans, D. A.; Fu, G. C. Chem. Rev., 1993, 93, 1307.)

The preparation of all four diastereomeric epoxides corresponding to 18 may be accomplished by using the methods described above, keeping in mind that Z-allylic alcohols are used to produce anti aldol products, and E-allylic alcohols yield syn aldols.

As a second exemplary embodiment of this aspect of the invention, the 2-triethysilyloxy analog of the allylic alcohol 17 is epoxidized with titanium tetraisopropoxide and t-BuOOH, without a chiral catalyst, to yield the all syn silyloxy epoxyalcohol (2S,3R,4R,5R)-5-(triethylsilyloxy)-2,3-epoxy-2-,4-dimethyl-1-octanol 30 as a 10:1 mixture to its diastereomer:

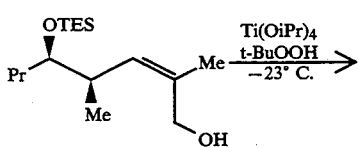

-continued

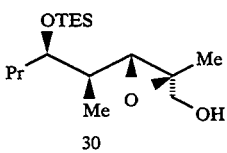
30

An epoxyalcohol such as 18 or 30 may be treated with a silyl reagent, preferably a trialkylsilyl triflate, to yield a polypropionate, with high enantiocontrol. The silyloxy groups of such a compound may be removed and replaced by hydroxyl groups, in the manner described above. Alternatively, the process (conversion to an allylic alcohol, epoxidation, and rearrangement) may be repeated to form longer polypropionates.

It has also been discovered that a silyloxy epoxyalcohol such as 18, 30, etc. can be converted into a chiral polypropionate using an alkyl or aryl lithium compound and a rare earth catalyst. Thus, alcohol 18' (which is the same as 18 except for the identity of the silyloxy group) is treated with (i) butyl lithium, and (ii) samarium diiodide, to yield the polypropionate (2S,3S,4S,5R)-5-triethylsilyloxy-3-hydroxy-2,4-dimethyloctanal:

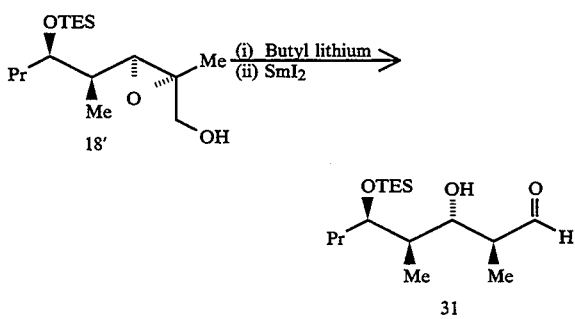

Though not bound by theory, it is believed that the alkyl lithium abstracts a proton from the alcohol, leaving the nucleophile R—O⁻, which attacks the samarium atom, which catalyzes the regioselective opening of the epoxide and the rearrangement to 31. The reaction may also be run using the samarium catalyst:

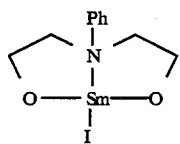

The following examples describe in detail syntheses illustrative of the present invention. It will be apparent to those skilled in the art that many modifications, both of materials and methods, may be practiced without departure from the purpose and intent of this disclosure.

EXAMPLES

All temperatures and boiling points (bp) are uncorrected and reactions were carried out under Argon (Ar) with the exclusion of moisture. Dichloromethane ($CH_2Cl_2$) was distilled from $CaH_2$. Tetrahydrofuran (THF) was distilled from sodium/benzophenone ketyl radical. Hexamethylphosphoramide (HMPA) was distilled under vacuum from $CaH_2$ prior to use. Titanium-(IV) isopropoxide (Ti(O-iPr)$_4$) was distilled under vacuum and stored frozen at $-23°$ C. under nitrogen ($N_2$). Diisopropyl tartrate ((+)- or (—)-DIPT) was distilled under vacuum and stored in a dessicator. Commercial t-butylhydroperoxide (TBHP) was dried over 4 Å molecular sieves (pellet form) for 2 days at 0° C. and titrated. (See Hanson, R. M.; Sharpless, K. B., J. Org. Chem. 1986, 51, 1922.)

Triethylsilyl trifluoromethanesulfonate (TESOTf), and t-butyldimethlysilyl trifluoromethanesulfonate (TBSOTf) were vacuum distilled through a jacketed Vigreaux column and stored under $N_2$ in Schlenk flasks. Diisopropylethylamine (DIPEA), triethylamine (TEA), and collidine were distilled from $CaH_2$ and stored under $N_2$. Boron trifluoride-etherate (BF$_3$-Et$_2$O) was stirred over $CaH_2$, distilled (67° C. at 43 mm Hg) with an excess of diethyl ether (Et$_2$O) and stored at $-23°$ C. under $N_2$. Boron tris(trifluoromethanesulfonate) (B(OTf)$_3$) was prepared by known procedures and distilled immediately before use. (See Olah, G. A.; Farooq, I.; Farnia, S. M. F.; Olah, J. A., J. Am. Chem. Soc. 1988, 110, 2560.) Powdered 4 Å molecular sieves were activated by heating to 120° C. in a vacuum oven (ca. 1 mm Hg) overnight and cooled under vacuum. Chromatography was conducted on 230-400 mesh silica gel ($SiO_2$), using hexanes (Hex), ethyl acetate (EtOAc), and $CH_2Cl_2$ as solvents. Butyraldyhde and chlorotriethylsilane (TESCl) were distilled before use. Potassium hexamethyldisilazide (KHMDS), dimethylaminopyridine (DMAP), t-butylchlorodimethylsilane (TBSCl), and lithium triethylborohydride (1.0M in THF, LiBEt$_3$H) were purchased from Aldrich Chemical Company and used directly. Bis(2,2,2-trifluoroethyl) ethyl 2-phosphonopropionate was made by a known procedure, dried by distillation, and stored at $-23°$ C. (See Still, W. C.; Gennari, C. Tetrahedron Lett. 1983, 24, 4405.) 18-Crown-6 was recrystallized from acetonitrile and evacuated for 3 days (0.01 mm Hg).

$^1$H and $^{13}$C nuclear magnetic resonance (NMR) were recorded on a Bruker AM360, AM500, ARX400 or ARX500 with tetramethylsilane as external standard. Enantiomeric purity were determined by reacting the substrates (ca. 0.05-0.1 mmol) in a sealed NMR tube with 750 μl of a 10% $C_6D_6$ in benzene solution (0.22M) of chiral phosphonamide for 1 day at 25° C. (See Alexakis, A.; Mutti, S.; Normant, J. F.; Mangeney, P. Tetrahedron Asymm. 1990, 1,437.) The diastereomeric $^{31}$P signals were then integrated and reported relative to 85% $H_3PO_4$ (0.00 ppm) as external standard. Infrared (IR) spectra were recorded on a Nicolet 510 FT-IR, Nicolet 205 FT-IR, or a Perkin-Elmer series 1600 spectrometer. Optical rotations were recorded on a Perkin-Elmer 243 Polanmeter and were run at ambient temperature. Isomeric ratios were determined on a Hewlett-Packard 5890 gas chromatograph/5970 Mass Selective Detector (GC-MS), with a 50 m capillary column, 1.0 ml/min Helium flow rate and selective ion monitoring. High resolution mass spectra (MS) were obtained on a VG Autospec at a resolution of 10000 (10% valley).

In the following examples, "ee" denotes enantiomeric excess, and "de" denotes diastereomeric excess.

Example 1

(E)-2-Methyl-2-hexen-1-ol (2)

This was prepared by a modified Bayliss-Hilman procedure using ethyl acrylate and DABCO, followed by acetylation and reduction with an ethoxyaluminum hydride reagent. (See Basavaiah, D.; Sarma, P. K. S. J. Chem. Soc., Chem. Commun. 1992, 955) to yield 4.732 g of 2 after distillation (bp 96° C. at 47 mm Hg, 51% from butyraldehyde): $^1$H NMR (CDCl$_3$, 360.134 MHz) δ:5.34 (1H, tq,J=7.22, 1.33 Hz), 3.93 (2H, d, J=0.74 Hz), 1.94 (2H, dq, J=8.00, 0.84 Hz), 1.73 (1H, br), 1.59 (3H, dd, J=0.35, 0.84 Hz), 1.29 (2H, sextet, J=7.45 Hz), and 0.84 (3H, t, J=7.39 Hz). $^{13}$C NMR (CDCl$_3$, 90.55 MHz) δ:134.7, 126.4, 69.0, 29.6, 22.6, 13.8, and 13.6. IR (thin film): 3380 (br), 2959 (s), 2929 (s), 2871 (s), 1458 (m), 1379 (m), 1222 (w), 1073 (s), 1046 (s), 1031 (s), 1000 (s), and 893 (w) cm$^{-1}$. High resolution MS (m/z): 96.0940, calcd for C$_7$H$_{12}$ 96.3843 (M-H$_2$O). Capillary GC-MS shows 96.6% (E) and 3.43% (Z).

Example 2

(Z)-2-Methyl-2-hexen-1-ol (12)

Method A: To bis(2,2,2-trifluoroethyl) ethyl 2-phosphonopropionate (1.2975 g, 3.75 mmol, 1.5 eq), 18-crown-6 (2.6770 g, 10.18 mmol, 4.05 eq) in 30 ml of THF at −42° C. under AR was added solid KHMDS (95% pure, 734 mg, 3.68 mmol, 1.4 eq). After 30 min, the solution was cooled to −78° C. and butyraldehyde (225 μl, 2.5 mmol) was added drop wise. The reaction was stirred for 8 h at −78° C. and −20° C. for 12 h when the solution was recooled to −78° C. and 1.0M LiBEt$_3$H in THF (10.0 ml, 10.0 mmol, 2.7 eq based on phosphonate) was added. The reaction was warmed to 25° C. over 4 h, and stirred an additional 10 h. Excess hydride was quenched with 2 ml of EtOAc, and after 10 min., the solution was poured onto 40 ml of distilled H$_2$O. The layers were separated and the aqueous phase extracted with pentane (4×25 ml). The combined organic phases were washed with brine (2×2 ml), dried over MgSO$_4$, concentrated and chromatographed (80 g SiO$_2$, 97% CH$_2$Cl$_2$/3% EtOAc) to yield 256.0 mg (2.24 mmol, 90%) of 12 as a clear oil.

Method B**: To a suspension of butyltriphenylphosphonium bromide (5.0742 g, 12.7072 mmol, 1.1 eq) in 50 ml of THF and 5 ml HMPA at 25° C. was added KHMDS (95%, 12.09 mmol, 1.05 eq) in one portion. After 10 min, the solution was cooled to −78° C. and 1-[(tetrahydropyranyl)-oxy]-2-propanone (1.80 g, 11.552 mmol) was added. The reaction was allowed to warm to 25° C. over 12 h, at which time 50 ml of saturated NH$_4$Cl was added. The slurry was poured onto 100 ml of pentane, shaken, and separated. The water phase was extracted with pentane (2×50 ml), and the combined organic phases washed with brine (3×20 ml), dried over MgSO$_4$, concentrated and chromatographed (400 g SiO$_2$, CH$_2$Cl$_2$, R$_f$=0.41) to yield 2.1133 g (92.3%) of the protected allylic alcohol. The product was then dissolved in 75 ml of 3:1 THF:H$_2$O, treated with 340 mg of p-toluenesulfonic acid, and refluxed for 12 h, at which time the solution was partitioned between 100 ml Et$_2$O and 100 ml H$_2$O. The layers were separated, the aqueous phase extracted with Et$_2$O (3×25 ml), and the combined organic extract washed with 5% NaHCO$_3$ (3×5 ml), brine (2×5 ml), dried over MgSO$_4$, concentrated and chromatographed (200 g SiO$_2$, 2.4% EtOAc/97.6% CH$_2$Cl$_2$) to yield 1.107 g of allylic alcohol 12 (91%, 84% overall). $^1$H NMR (CDCl$_3$, 360.134 MHz) δ:5.20 (1H,t,J=7.48 Hz), 4.02 (2H,s), 2.01 (1H, br), 1.93 (2H, qd,J=7.30, 1.11 Hz), 1.70 (3H,q, J=1.29 Hz), 1.26 (2H, sextet, J=7.38 Hz), and 0.80 (3H,t, J=7.37 Hz). $^{13}$C NMR (CDCl$_3$, 90.55 MHz) δ:134.3, 128.3, 61.3, 29.5, 23.0, 21.0, and 13.6. Bp=99° C. at 55 mm Hg. Capillary GC-MS shows 97.22% (Z) and 2.78% (E).

**See Sreekumar, C.; Darst, K. P.; Still, W. S. *J. Org. Chem.* 1980, 45, 4260.

Example 3

(E)-4-Phenyl-2-methyl-2-buten-1-ol (20)

This was synthesized according to a known procedure in 79 % yield. $^1$H NMR (CDCl$_3$, 500.135 MHz) δ:7.1–7.3 (5H, m), 5 57 ($^1$H, tq, J=7.39, 1.39 Hz), 4.00 (2H, s), 3.35 (2H, d,J=7.31 Hz), 1.73 (3H, q,J=0.36 Hz), and 1.40 (1H, br). $^{13}$C NMR (CDCl$_3$, 90.55 MHz) δ:140.9, 135.6, 128.4, 128.2, 125.9, 124.6, 68.6, 33.8, and 13.7. IR (thin film): 3332 (br), 3084 (m), 3061 (m), 3026 (s), 2975 (m), 2914 (s), 2959 (s), 1602 (m), 1494 (s), 1453 (s), 1072 (m), 1029 (m), 1016 (s), 866 (w), 741 (s), and 698 (s) cm$^{-1}$. High Resolution MS (m/z): 162. 1029, calcd for C$_{11}$H$_{14}$O 162.1045. Capillary GC-MS shows 90.8 % (E) and 9.2 % (Z).

Example 4

(2S,3S)-2-Methyl-3-propyloxiranementhanol (8)

This is a representative procedure for the synthesis of epoxy alcohols. (See Hanson, R. M.; Sharpless, K. B., *J. Org. Chem.* 1986, 51, 1922.) (+)-DIPT (317.0 mg, 1.35 mmol, 0.17 eq) was weighed into a dry, 3 neck, 25 ml round bottom flask equipped with 500 mg of powdered 4 Å mol. sieves. The flask was flushed with Ar, fitted with an overhead stirrer and 10 ml of CH$_2$Cl$_2$ was added. The solution was cooled to −10° C., and treated successively with Ti(O-iPr)4 (288 μl, 0.97 mmol, 0.12 eq) and 4.25M TBHP (3.2 ml, 13.39 mmol, 1.7 eq). After 15 min, the solution was cooled to −32° C., and allylic alcohol 2 (891.2 mg, 7.80 mmol) in 2.5 ml CH$_2$Cl$_2$ was added via syringe pump over 25 min. At the completion of the reaction (ca. 2 h), the cooling bath was removed, 3 ml of water was added and the mixture vigorously stirred until a clear solution resulted (2–6 h). The tartrate was then hydrolyzed by stirring the solution for an additional 3 h with 1 ml of 30% NaOH/saturated NaCl at which time two phases were apparent. The mixture was transferred into 2–15 ml centrifuge tubes, centrifuged and the CH$_2$Cl$_2$ layer drawn out via syringe. The aqueous phase was extracted in a like fashion (4×5 ml each tube) and the combined CH$_2$Cl$_2$ extracts were stirred over MgSO$_4$, filtered through a pad of Celite, concentrated and chromatographed (100 g SiO$_2$, 80% CH$_2$Cl$_2$/20% EtOAc, R$_f$=0.31) to yield 826.2 mg (7.35 mmol, 94%) of epoxy alcohol 8 as a clear oil. $^1$H NMR (CDCl$_3$, 360.134 MHz) δ 3.66 (1H, dd, J=12.2, 4.68 Hz), 3.54 (1H, dd, J=12.3, 8.3 Hz), 3.02 (1H, t, J=5.4 Hz), 2.06 (1H, dd, J=8.3, 4.8 Hz), 1.6–1.4 (4H, m), 1.26 (3H, s), and 0.96 (3H, t,J=7.3 Hz). $^{13}$C NMR (CDCl$_3$, 90.55 MHz) δ 65.4, 60.8, 60.0, 30.1, 19.7, 14.2, and 13.9. IR (thin film): 3426 (br), 2961 (s), 2932 (s), 2874 (s), 1466 (s), 1383 (m), 1074 (s), 1036 (s), 889 (m), and 683 (w) cm$^{-1}$. High resolution MS (m/z): 130.0998, calcd for C$_7$H$_{14}$O$_2$ 130.0994. [α]$_D$ =−25.9° (c=1.05, CH$_2$Cl$_2$). Bp=49.5° C. at 0.90 mm Hg. −P NMR (10% C$_6$D$_6$ in benzene, 145.786 MHz) δ135.2 (98%) and 137.2 (2%), 96% ee.

Example 5

(2R,3R)-2-Methyl-3-propyloxiranemethanol (3)

Using the same procedure for the preparation of 8 from (−)-DIPT and allylic alcohol 2 gave 3 in 94% yield. The $^1$H NMR, $^{13}$C NMR, IR and high resolution MS were identical to 8. [α]$_D$+26.0° (c=1.05, CH$_2$Cl$_2$). −P NMR (10% C$_6$D$_6$ in benzene, 145.786 MHz) δ 133.5 (2.7%) and 137.2 (97.3%), 95.5% ee.

Example 6

(2R,3S)-2-Methyl-3-propyloxiranemethanol (13)

Using the same procedure for the preparation of 8, (−)-DIPT, alcohol 12, with a 36 h reaction time, gave 13 in 81% yield. $^1$H NMR (CDCl$_3$, 360.134 MHz) δ 3.57 (1H, d, J=11.80 Hz), 3.51 (1H, d, J=11.80 Hz), 2.73 (1H, t, J=6.19 Hz), 2.00 (1H, br), 1.5–1.3 (4H, m), 1.27 (3H, s), and 0.84 (3H, t, J=7.30 Hz). $^{13}$C NMR (CDCl$_3$, 90.55 MHz) δ 64.8, 63.9, 60.8, 30.0, 20.1, 19.9, and 13.9. IR (thin film): 3436 br), 2965 (s), 2938 (s), 1466 (m), 1381 (m), 1300 (w), 1267 (w), 1175 (m), 1044 (s), 889 (m), and 853 (m) cm$^{-1}$. High resolution MS (m/z): 130.0997, calcd for C$_7$H$_{14}$O$_2$ 130.0994. [α]D=−14.5° (c=0.615, CH$_2$Cl$_2$). −P NMR (100% C$_6$D$_6$ in benzene, 145.786 MHz) δ:133.5 (92.8%) and 132.4 (7.4%), 85.5% ee.

Example 7

(2R,3R)-2-Methyl-3-propyloxiranemethanol (15)

Using the same procedure as for the preparation of 13, (+)-DIPT and allylic alcohol 12 gave 15 in 79% yield. $^1$HNMR, $^{13}$C NMR IR and high resolution MS are identical to 13. [α]D=+13.9° (c=1.35, CH$_2$Cl$_2$). −P NMR (10% C$_6$D$_6$ in benzene, 145.786 MHz) δ:132.4 (93.2%) and 133.5 (6.8%), 86.5% ee.

Example 8

(2R,3R)-2-Methyl-3-phenylmethyloxiranemethanol (10)

Using the same procedure as for the preparation of 8, (−)-DIPT and allylic alcohol 20 gave 75% yield of epoxy alcohol 10. $^1$H NMR (CDCl$_3$, 360.134 MHz) δ:7.2–7.4 (5H, m), 3.69 (1H, dd, J=4.66, 12.29 Hz), 3.58 (1H, dd, J=8.20, 12.29 Hz), 3.28 (1H, t, J=6.35 Hz), 2.96 (1H, dd, J=6.46, 14.76 Hz), 2.86 (1H, dd, J=6.25, 14.77 Hz), 1.92 (1H, dd, J=8.37, 4.72 Hz), and 1.41 (3H, s), $^{13}$C NMR (CDCl$_3$, 99.55 MHz) δ:137.6, 128.68, 128.64, 126.61, 65.3, 61.3, 60.2, 34.6, and 14.4. IR (thin film): 3424 (br), 3086 (w), 3062 (w), 3028 (m), 2997 (w), 2984 (m), 2926 (s), 2868 (m), 1604 (w), 1495 (s), 1454 (s), 1384 (m), 1072 (m), 1063 (s), 891 (w), 853 (w), 741 (m), and 700 (s) cm$^{-1}$. [δ]D=+22.1° (c=2.65, CHCl$_3$).

Example 9

(2R,3R)-2-[(t-butyldimethylsilyloxy)methyl]-2-methyl-3-propyloxirane (4)

Alcohol 3 (51.1 mg, 0.3925 mmol) in 3 ml of CH$_2$Cl$_2$ was treated successively with DIPEA (102 μl, 0.5888 mmol, 1.5 eq), DMAP (1 crystal), and TBSCl (77 mg, 0.5103 mmol, 1.3 eq) and refluxed for 12 h. The solution was poured onto 20 ml of 0.2M pH 7 phosphate buffer and 30 ml of low boiling petroleum ether, shaken, and separated. The aqueous phase was extracted with petroleum ether (3×10 ml), washed with pH 7 buffer (1×10 ml), H$_2$O (1×5 ml), brine (1×5 ml), dried over MgSO$_4$, and concentrated to give 86.0 mg of 4 as a clear oil (89.6%). $^1$H NMR (CDCl$_3$, 360.134 MHz) δ:3.57 (1H, d, J=11.15 Hz), 3.53 (1H, d, J=11.17 Hz), 2.82 (1H, t, J=5.70 Hz), 1.6–1.4 (4H, m), 1.25 (3H,s), 0.95 (3H, t, J=7.13 Hz), 0.87 (9H, s), 0.04 (3H, s), and (3H, s). $^{13}$C NMR (CDCl$_3$, 90.55 MHz) δ:68.0, 61.0, 60.8, 30.2, 25.8, 19.7, 18.3, 14.1, 13.9, and −5.4. IR (thin film): 2959 (s), 2930 (s), 2859 (s), 1473 (m), 1464 (m), 1382 (w), 1362 (w), 1253 (m), 1103 (s), 838 (s), 778 (s), and 667 (w) cm$^{-1}$. [δ]D=+4.9° (c=2.62, CH$_2$Cl$_2$).

Example 10

(2R,3R)-2-[(triethylsilyloxy)methyl]-2-methyls-3-propyloxirane (19)

Epoxy alcohol 3 (714.5 mg, 5.4882 mmol), was weighed into a dry, 50 ml, 1 neck round bottom flash equipped with a magnetic stirbar. The flask was flushed with Ar, treated successively with 30 ml of CH$_2$Cl$_2$, DIPEA (1.4 ml, 8.2323 mmol, 1.5 eq), and DMAP (ca. 50 mg). TESCl was added quickly and a mildly exothermic reaction ensued. After 1 h, the mixture was poured onto 100 ml of petroleum ether and 50 ml of 0.2M pH 7 phosphate buffer. The layers were separated, extracted with petroleum ether (2×50 ml), washed with 0.2M pH 7 phosphate buffer (1×10 ml), brine (1×10 ml), dried over MgSO$_4$, concentrated and distilled via short path (bp=72°–75° C. at 0.09 mm Hg) to give 1.3055 g of pure silyl epoxide 19 (97.3%). $^1$H NMR (CDCl$_3$, 500.135 MHz) δ:3.58 (1H, d, J=11.11 Hz), 3.52 (1H, d, J=11.10 Hz), 2.80 (1H, t, J=5.99 Hz), 1.6–1.4 (4H, m), 1.24 (3H, s), 1.0–0.9 (9H, m), and 0.60 (9H, q, J=7.82 Hz). $^{13}$C NMR (CDCl$_3$, 90.55 MHz) δ:67.7, 61.0, 60.8, 30.3, 19.8, 14.2, 13.9, 6.7, and 4.3. IR (thin film): 2957 (s) 2912 (s), 2876 (m), 1458 (m), 1416 (w), 1381 (m), 1240 (m), 1101 (s), 1007 (m), 820 (m), and 745 (s) cm-1. High resolution MS (m/z): 215.1456, calcd for C$_{11}$H$_{23}$O$_2$Si 215.1467 (M-C$_2$H$_5$). [δ]D=+3.7° (c=0.90, CH$_2$Cl$_2$).

Example 11

(2R,3R)-3-[t-Butyldimethylsilyloxy)-2-methylhexanal (16)

This is a representative procedure for the rearrangement of epoxy alcohols with trialkylsilyl trifluoromethanesulfonates. Epoxy alcohol 15 (74.3 mg, 0.4647 mmol) was dissolved in 4.0 ml of CH$_2$Cl$_2$, treated with 100 mg of 4 Å powdered molecular sieves, DIPEA (129 μl, 0.7419 mmol, 1.3 eq) and cooled to −42° C. TBSOTf (157.2 μl, 0.6849 mmol, 1.3 eq) was then added drop wise and stirred for 80 min at which time the solution was poured onto 20 ml of Et$_2$O and shaken with 5 ml of pH 5.5 phosphate buffer. The layers were separated and the aqueous phase extracted with Et$_2$O (2×5 ml). The combined organic phases were washed with H$_2$O (3×2 ml), 5% NaHCO$_3$ (2×2 ml), brine (1×2 ml), dried over MgSO$_4$ and the solvent evaporated to yield 132.0 mg of aldehyde 16 (slight contamination of silanol, 95%+yield). $^1$H NMR (CDCl$_3$, 360.134 MHz) δ:9.67 (1H, d, J=2.35 Hz), 3.89 (1H, q, J=5.40 Hz), 2.44 (1H, qdd, J=7.02, 5.40, 2.35 Hz), 1.5–1.3 (4H, m), 1.02 (3H, d, J=7.02 Hz), 0.86 (3H, t, J=7.31 Hz), 0.82 (9H, s), 0.01 (3H, s,), and −0.01 (3H, s). $^{13}$C NMR (CDCl$_1$, 90.55 MHz) δ:205.0, 73.2, 51.1, 37.0, 25.6, 18.01, 17.99, 14.2, 10.3, −4.3 , and −4.8. IR (thin film): 2959 (s), 2934 (s), 2859 (s), 1727 (s), 1472 (s), 1464 (s), 1362 (m), 1256 (s), 1125 (s), 1090 (s), 1074 (s), 1038 (s), 1007 (m), 889 (w), 837 (s), and 775 (s) cm$^{-1}$. High resolution MS (m/z): 187.1161, calcd for C$_9$H$_{19}$O$_2$Si 187.1154 (M-C$_4$H$_9$). [α]$_D$=−18.4° (c=1.43, CH$_2$Cl$_2$). $^1$H NMR integration of δ 3.89 and the contaminating diastereomer at δ 3.89 and the contaminating diastereomer at δ 4.05 indicated a 20:1 ratio.

Example 12

(2S,3S)-3-(t-Butyldimethylsilyloxy)-2-methylhexanal (14)

Epoxy alcohol 13, 1.25 eq TBSOTf, and 1.30 eq DIPEA were reacted as in the preparation of 16 to give the crude aldehyde 14 in 95% +yield. $^1$H NMR, $^{13}$C NMR, IR, and high resolution MS are identical to 16. [δ]D= +19.3° (c=1.10, CH$_2$Cl$_2$). $^1$H NMR integration of δ 9.67 and the contaminating diastereromer at δ 9.71 indicated a >50:1 ratio.

Example 13

(2S,3R)-3-(t-butyldimethylsilyloxy)-2-methylhexanal (5)

Epoxy alcohol 4, 1.3 eq TBSOTf, and 1.35 eq DIPEA were reacted as in the preparation of 16 to give crude aldehyde (>50:1 de, 95%+) which was then chromatographed (2% EtOAc/97% Hex/1% TEA) to give 5 in 78% yield. $^1$H NMR (CDCl$_3$, 500.135 MHz) δ:9.71 (1H, d, J=0.90 Hz), 4.05 (1H, dt, J=10.10, 3.50 Hz), 2.83 (1H, qdd, J=6.9, 3.5, 0.9 Hz), 1.6–1.2 (4H, m), 0.99 (3H, d, J=6.94 Hz), 0.86 (3H, t, J=7.27 Hz), 0.80 (9H, s), 0.06 (3H, s), and 0.01 (3H, s). $^{13}$C NMR (CDCl$_3$, 90.55 MHz) δ:205.5, 71.9, 51.2, 36.8, 25.7, 18.9, 17.9, 14.1, 7.6, −4.3, and −4.7. IR (thin film): 2959 (s), 2932 (s), 2859 (s), 1728 (s), 1472 (m), 1464 (m), 1389 (w), 1362 (w), 1254 (s) 1140 (m), 1105 (m), 1073 (m), 1034 (s), 837 (s), and 775 (s) cm$^{-1}$. High resolution MS (m/z): 187.1155, calcd for C$_9$H$_{19}$O$_2$Si 187.1154 (M-C$_4$H$_9$). [α]$_D$= +46.1° (c=1.0, CH$_2$Cl$_2$). $^1$H NMR integration of δ 9.71 and the contaminating diastereomer at δ 9.67 indicated a 96:4 ratio.

Example 14

(2R,3S)-3-(t-Butyldimethylsilyloxy)-2-methylhexanal (9)

Epoxy alcohol 8, 1.75 eq TBSOTf, and 1.80 eq DIPEA were reacted as in the preparation of 16 to give crude aldehyde (>50:1 de) which was then chromatographed (2% EtOAc/97% Hex/2% TEA) to give 9 in 87% yield. $^1$H NMR, $^{13}$C NMR, IR, and high resolution MS were identical to 5. [δ]D= −45.3° (c=1.01, CH$_2$Cl$_2$). $^1$H NMR integration of δ 9.72 and the contaminating diastereomer at δ 9.67 indicated a 91.8:8.2 ratio after chromatography.

Example 15

(2S,3R)-3-(Triethylsilyloxy)-2-methyl-4-phenylbutanal (11)

Epoxy alcohol 10, 1.2 eq of TESOTf, and 1.5 eq of collidine were reacted as in the preparation of 16 give 80% of aldehyde 11. $^1$H NMR (CDCl$_3$, 500.35 MHz) δ:9.64 (1H, d J=0.77 Hz), 7.30–7.05 (5H,m) 4.37 (1H, J=3.06, 10.40 Hz), 2.76 (1H, d J=6.64 Hz), 2.75 (2H, d J=7.42 Hz), 2.27 (1H, qdd, J=7.00, 3.38, 0.77 Hz), 1.10 (3H, d, J=7.04 Hz), 0.95–0.75 (6H, m), 0.6–0.4 (9H, m). $^1$H NMR integration of δ 9.64 to the contaminant δ 9.71 indicated a 93.6:6.4 ratio.

Example 16

(2S,3S)-3-(Triethylsilyloxy)-2-methylhexanal (22)

Epoxy alcohol 13, 1.4 eq TESOTf, and 1.5 eq of collidine were reacted as in the preparation of 16 to give 95%+yield (<20:1 de) of crude aldehyde 22 which was chromatographed (SiO$_2$, 3% EtOAc/96% Hex/1% TEA) to give 85% of 22. $^1$H NMR (CDCl$_3$, 500.135 MHz) δ:9.68 (1H, d, J=2.37 Hz), 3.89 (1H, q, J=5.03 Hz), 2.43 (1H, qdd, J=6.95, 5.03, 2.30 Hz), 1.5–1.2 (4H, m), 1.02 (3H, d, J=6.95 Hz), 0.89 (6H, t J=8.0 Hz), 0.85 (3H, t, J=7.14 Hz), and 0.54 (9H, q, J=7.80 Hz). $^{13}$C NMR (CDCl$_3$, 90.55 MHz) δ:205.1, 73.3, 51.3, 37.2, 18.1, 14.1, 10.3, 6.4, and 5.1. IR (thin film): 2957 (s), 2938 (s), 2912 (s), 2877 (s), 1726 (s), 1459 (s), 1415 (w), 1379 (w), 1239 (m), 1155 (w), 1074 (s), 1038 (m), 1005 (w), and 741 (s) cm$^{-1}$. high resolution MS (m/z): 215. 1467, calcd for C$_{11}$H$_{23}$O$_2$Si 215.1467 (M-C$_2$H$_5$). [α]$_D$= +14.7° (c=1.89, CH$_2$Cl$_2$). $^1$H NMR integration of δ 9.69 to δ 9.72 indicated a 90.3:9.7 ratio.

Example 17

(2S,3R)-3-(Triethylsilyloxy)-2-methylhexanal (21)

Method A: Silyl epoxide 19 (97.8 mg, 0.40 mmol) was dissolved 1.3 ml of CH$_2$Cl$_2$ and treated successively with 34 mg of powdered 4 Å molecular sieves and DIPEA (21 μl, 0.12 mmol, 0.30 eq). The solution was cooled to −42° C. and treated with TESOTf (22 μl, 0.10 mmol). After 60 min, the solution was poured onto Et$_2$O (20 ml) and 10 ml of pH 5.5 buffer. The layers were separated, extracted with Et$_2$O (3×5 ml), washed with H$_2$O (3×1 ml), 5% NaHCO$_3$ (2×1 ml), brine (1×5 ml), dried over MgSO$_4$, and concentrated to yield 98.5 mg of virtually pure aldehyde 21. $^1$H NMR shows <50:1 de.

Method B: Silyl epoxide 19 (143.9 mg, 0.5887 mmol) was dissolved in 5 ml of CH$_2$Cl$_2$ and cooled to −78° C. in an inert atmosphere. BF$_3$-Et$_2$O (72 μl, 0.59 mmol, 1.00 eq) was added and the solution stirred for 1 h. Then 2 ml of saturated Na$_2$CO$_3$ was added and the cooling bath removed. After reaching 25° C., the layers were separated, extracted with Et$_2$O (4×1 ml), washed with H$_2$O (3×1 ml), brine (2×1 ml), dried over MgSO$_4$, concentrated and chromatographed (70 g SiO$_2$, 95% Hex/1% TEA/4% EtOAc, R$_f$=0.50) to yield 125.0 mg of aldehyde 21 (86%, 94:6 de).

Method C: To a stirring solution of silyl epoxide 19 (37.0 mg, 0.1514 mmol), 23 mg of mol. sieves, and DIPEA (2.6 μl, 15.1 μmol, 0.10 eq) in 1.5 ml of CH$_2$Cl$_2$ at −42° C. was added 0.2M TESOTf-B(OTf)$_3$ (37.8 μl, 7.6 μmol, 0.05 eq) and the solution turned pale yellow. (Note: A solution of TESOTf in CH$_2$Cl$_2$ was added to freshly prepared B (OTf)$_3$ analogous to the preparation of TMSOTf-B (OTf)$_3$. See Davis, A. P.; Jaspars, M. Angew. Chem. Int. Ed. Engl., 1992, 31, 470.) After 10 min, 100 μl of DIPEA was added (color fades) followed by 2.0 ml of 0.2M pH 7 phosphate buffer. The mixture was poured onto 5 ml of 5% NaHCO$_3$, separated, extracted with Et$_2$O (2×5 ml), brine (1×1 ml), dried over MgSO$_4$ and concentrated to give 36.4 mg of aldehyde 21 (95%+, >20:1 de). $^1$H NMR (CDCl$_3$, 500.135 MHz) δ:9.71 (1H, d J=1.01 Hz), 4.06 (1H, dt J=10.98, 3.65 Hz), 2.37 (1H, qdd, J=6.96, 3.65, 1.00 Hz), 1.5–1.15 (4H, m), 0.99 (3H, d, J=6.96 Hz), 0.90–0.80 (9H, m), and 0.52 (9H, q, J=7.83 Hz). $^{13}$C NMR (CDCl$_3$, 90.55 MHz) δ:205.4, 72.0, 51.4, 36.9, 19.0, 14.1, 7.7, 6.8 and 5.1. IR (thin film): 2957 (s), 2912 (s), 2876 (s), 1728 (s), 1459 (m), 1414 (m), 1379 (w), 1239 (m), 1105 (m), 1074 (m), 1035 (m), 1006 (m) and 740 (s) cm$^{-1}$. High resolution MS (m/z): 215.1447, calcd for C$_{11}$H$_{23}$O$_2$Si 215.1467 (M-C$_2$H$_5$). [α]$_D$= +36.6° (C=1.09, CH$_2$Cl$_2$).

Example 18

(4R,5R)-(Z)-5-(t-Butyldimethylsilyloxy)-2,4-dimethyl-2-octen-1-ol (17)

Bis (2,2,2-trifluoroethyl) ethyl 2-phosphonopropionate (173.8 mg, 0.5021 mmol, 1.5 eq) was weighed into a 25 ml Schlenk flask, flushed with Ar, dissolved in 10 ml of THF, cooled to −42° C. It was then treated with 0.75M KHMDS in THF (600 μl, 0.45 mmol, 1.35 eq). After 1 h, 18-crown-6 (439 mg, 1.663 mmol, 5.0 eq) was added and the solution cooled to −78° C. Aldehyde 5 (freshly prepared, 81.3 mg, 0.3326 mmol) in 250 μl THF was added. The reaction was stirred for 4 h at −78° C., at −23° C. for 12 h, then was recooled to −78° C. and 1.0M LiEt$_3$BH in THF was added (2.0 ml, 2.0 mmol, 4.4 eq based on phosphonate). The temperature gradually warmed to 25° C. over 4 h and stirred an additional 8 h when 500 μl of EtOAc was added. The solution was poured onto 10 ml of 0.2M pH 7 phosphate buffer, and extracted with 3:1 pentane:Et$_2$O (3×10 ml). The extracts were washed with 5% NaHCO$_3$ (2×1 ml), brine (1×1 ml), dried over MgSO$_4$, concentrated and chromatographed (80 g SiO$_2$, 1% TEA/CH$_2$Cl$_2$) to give 68.4 mg of isometrically pure alcohol 17 (72%). $^1$H NMR (CDCl$_3$, 360.134 MHz) δ:5.09 (1H, d J=9.89 Hz), 4.06 (1H, d, J=11.65 Hz), 3.96 (1H, d, J=11.65 Hz), 3.41 (1H,q, J=4.62 Hz), 2.47 (1H, m), 1.74 (3H, d, J=1.45 Hz), 1.60 (1H, br), 1.4–1.15 (4H, m), 0.86 (3H, d, J=6.84 Hz), 0.83 (9H, s), 0.83 (3H, s). $^{13}$C NMR (CDCl$_3$, 90.55 MHz) δ:134.0, 132.0, 76.6, 61.7, 37.4, 26.0, 21.7, 18.6, 18.3, 17.1, 14.4, −4.3, −4.4. IR (thin film): 3333 (br), 2959 (s), 2932 (s), 2858 (s), 1462 (m), 1377 (w), 1256 (m), 1068 (m), 1032 (s), 1005 (s), 837 (s), and 773 (s) cm$^{-1}$. High resolution MS (m/z): 229.1613, calcd for C$_{12}$H$_{25}$O$_2$Si 229.1624 (M-C$_4$H$_9$). [α]$_D$=+6.25° (c=1.68, CH$_2$Cl$_2$).

Example 19

(2R,3S,4S,5R)-5-(t-Butyldimethylsilyloxy)-2,3-epoxy-2,4-dimethyl-1-octanol (18)

Allylic alcohol 17 (200.0 mg, 0.7005 mmol) was dissolved in 5 ml of CH$_2$Cl$_2$ and cooled to −5° C. under Ar with a brine/ice bath. Then, m-CPBA (65% purity, 223 mg, 0.8406 mmol, 1.2 eq) in 2 ml CH$_2$C$_2$ was added drop wise. Within 10 min, the acid byproduct precipitated, and after 30 min the reaction was complete. The mixture was diluted to 40 ml with pentane and washed vigorously with 10% NaOH (2×10 ml), H$_2$O (2×2 ml), 5% NaHCO$_3$ (1×2 ml), brine (2×1 ml), dried over MgSO$_4$, and concentrated to give a 12:1 mixture of epoxy alcohol 18 and its diastereomer. The mixture was chromatographed (100 g SiO$_2$, 4% EtOAc/96% CH$_2$Cl$_2$) to yield 189.0 mg of 18 (90%). $^1$H NMR (CDCl$_3$, 360.134 MHz) δ:3.70 (1H, dt, J=3.48, 9.11 Hz), 3.60 (2H,m), 2.71 (1H, d, J=9.60 Hz), 1.99 (1H, br), 1.35–1.45 (3H, m), 1.31 (3H,s), 1.25–1.1 (2H,m), 0.83–0.79 (15H, br) and −3.4 (6H, s). $^{13}$C NMR (CDCl$_3$, 90.55 MHz) δ 72.6, 67.0, 63.9, 61.0, 37.3, 36.1, 25.9, 20.5, 18.4, 18.1, 14.3, 10.2–4.1, and −4.8. IR (thin film): 3430 (br), 2957 (s), 2928 (s), 2857 (s), 1462 (s), 1379 (s), 1254 (s), 1030 (s), 937 (m), 891 (m), 837 (s), and 772 (s) cm$_{-1}$. High resolution MS (m/z): 245. 1583, calcd for C$_{12}$H$_{25}$O$_3$Si 245. 1572 (M-C$_4$H$_9$). [δ]D=−12.7° (c=0.97, CH$_2$Cl$_2$).

Example 20

(2S,3R)-3-(Triethylsilyloxy)-2-methylhexan-1-ol (24)

Aldehyde 21 (87.0 mg, 0,3559 mmol) in 2.0 ml of methanol at 0° C. was treated with sodium borohydride (6.4 mg, 0.1692 mmol, 1.9 eq hydride) for 1 h at which time 2.0 ml of 0.05M pH 7.0 phosphate buffer was added with simultaneous removal of cooling bath Upon reaching 25° C., the slightly turbid mixture was extracted with Et2O (3×10ml), washed with brine (2×1 ml), dried over MgSO$_4$, concentrated and chromatographed (35 g SiO$_2$, 2% EtOAc/1% TEA/97% CH$_2$C$_2$,Rf=0.18) to give 65.7 mg of alcohol 23 (75%) as a clear oil. $^1$H NMR (CDCl$_3$,360.134 MHz) δ 3.73 (1H,m), 3.64 (1H,t,J=4.63 Hz), 3.47 (1H,m), 2.77 (1H,br), 1.88 (1H,m), 1.45–1.30 (3H,m), 1.20–1.10 (1H,m), 0.90 (9H,t,J=7.90 Hz), 0.86 (3H,t,J=7.18 Hz), 0.75 (3H,d,J=7.07 Hz), and 0.56 (6H, q,J=7.90 Hz). $^{13}$C NMR (CDCl$_3$, 90.55 MHz) δ 76.1, 66.2, 39.5, 34.6, 19.5, 14.2, 11.9, 6.8, and 5.1. IR (thin film): 3380 (br), 2958(s), 2937(s), 2913(s), 2877(s), 1459(w), 1415(w), 1380(w), 1239(w) 1100(m), 1073(m), 1032(m), 1007(m), 739 (m), and 726 (m) cm$^{-1}$. High Resolutions MS (m/z) 217. 1622, calcd for C$_{11}$H$_{25}$O$_2$Si 217.1624 (M-C$_2$H$_5$).

Example 21

(2S,3S)-3-(Triethylsilyloxy)-2-methylhexan-1-ol (25)

Aldehyde 22 and 2.5 eq sodium borohydride were reacted as in the preparation of 24 to give 47% alcohol 25 after chromatography (35 g SiO$_2$, 2% EtOAc/1% TEA/97% CH$_2$Cl$_2$, Rf=0.34). $^1$H NMR (CDCl$_3$, 360.134 MHZ) δ:3.70 (1H, br d, J=11.02 Hz), 3.65 (1H,q,J=5.45 Hz), 3.46 (1H, br d), 2.85 (1H, br), 1.68 (1H,m), 1.46 (2H,m), 1.27 (2H,m), 092 (3H,d,J=5.45 Hz), 3.46 (1H, br d), 2.85 (1H, br), 1.68 (1H,m), 1.46 (2H,m), 1.27 (2H,m), 0.92 (3H,d,J=7.07 Hz), 0.90 (9H,t,J=7.90 Hz), 0.85 (3H,t,J=7.30 Hz), and 0.56 (6H,q,J=7.90 Hz). $^{13}$C NMR (CDCl$_3$, 90.55 MHz) δ:77.6, 65.7, 38.0, 37.3, 18.0, 14.6, 14.3, 6.8, and 5.0. IR (thin film): 3400 (br) 2958(s), 2913(s), 2876(s), 1458(m), 1415(w), 1379(w), 1239(m), 1119(w), 1079(sJ), 1007 (s), 784 (w), 739 (s), and 727 (s) cm$^{-1}$. High resolution MS (m/z): 217.1624, calcd for C$_{11}$H$_{25}$O$_2$Si 217.1621 (M-C$_2$H$_5$).

Example 22

(4R,5R)-2,2,5-trimethyl-4-propyl-1,3-dioxane (28)

Alcohol 24 (100.0 mg, 0.4057 mmol) was dissolved in 2.0 ml of Et$_2$O and treated with 676 mg of tetrabutylammonium fluoride on silica (1.2 mmol/g, 0.8112 mmol, 2.0 eq) and stirred at 25° C. for 3h at which time alumina (acidic, ca. 1 g) was added. The slurry was filtered through a pad of Celite, concentrated and chromatographed (25 g SiO$_2$, 60% CH$_2$Cl$_2$/40% EtOac) to yield 27.9 mg of diol 26 (52%) which was protected for characterization. Diol 26 (27.9 mg, 0.211 mmol) was dissolved in 5.0 ml of THF, and treated with 2,2-dimethoxypropane (64 μl, 0.5159 mmol, 2.0 eq) and a crystal of p-toluenesulfonic acid. After 67 h at 25° C., 200 mg of Na$_2$CO$_3$ was added. The mixture was poured onto 7.0 ml of 0.10M pH 7.0 phosphate buffer, extracted with Et$_2$O (3×10 ml), washed with H$_2$O (1×1 ml), 5% NaHCO$_3$ (2×1 ml), brine (1×1 ml), dried over MgSO$_4$ and concentrated to give 30.0 mg of acetonide 28 as a clear liquid (89%). $^1$H NMR (CDCl$_3$, 360.134 MHz) δ 4.04 (1H,dd,J=11.56, 2.90 Hz), 3.86 (1H,ddd,J=10.40, 5.29, 2.52 Hz), 3.52 (1H,dd,J=11.44, 0.68 Hz), 1.37 (3H, s), 1.33 (3H, s), 1.45–1.1 (5H,m), 0.99 (3H, d,J=6.92 Hz), and 0.86 (3H,t,J=7.08H). $^{13}$C NMR (CDCl$_3$, 90.55 MHz) δ:72.0, 71.2, 67.0, 35.0, 31.7, 29.8, 19.1, 18.5, 14.0, and 10.5. IR (thin film): 2957(m), 2924(s), 2855(m), 1732(br), 1458(m), 1377(w), 1262(m), 1179 9(w), 1074(w), and 800(w) cm$^{-1}$.

Example 23

(4S,5R)-2,2,5-trimethyl-4-propyl-1,3-dioxane (29)

Alcohol 25 was converted to the intermediate diol 27 (85%) and acetonide 29 (85%) as in the preparation of 28 $^1$H NMR (CDCl$_3$, 360.134 MHz) δ:3.62 (1H,dd J=6.69 Hz). $^{13}$C NMR (CDCl$_3$, 90.55 MHz) δ:74.6, 72.1, 66.2, 35.1, 34.0, 29.8, 19.1, 18.1, 14.0, and 12.7. IR (thin film): 2957(m), 2924(s), 2853(m), 1728(br), 1462(m), 1379(m), and 1261 (m) cm$^{-1}$.

Example 24

(2S,3S,4R,5R)-5-(Triethylsilyloxy)-2,3-epoxy-2,4-dimethyl-1-octanol (30)

To a solution of (4R,5R)-(Z)-2,4-dimethyl-5(triethylsilyloxy)oct-2-ene-1-ol (124.0 mg, 0.4328 mmol) and 30 mg of powdered molecular sieves in 4.0 ml of CH$_2$Cl$_2$ at −42° C. was added (Ti(O-iPr)$_4$ (146 µl, 0.6491 mmol, 1.5 eq) and the reaction was kept at −23° C. for 3 wk after which 2.0 ml of ½ saturated Rochelle's salt was added and stirred overnight. The layers were separated, extracted with Et$_2$O (3×15 ml), washed with H$_2$O (2×1 ml), 5% NaHCO$_3$ (1×5ml), brine (1×2 ml) dried over MgSO$_4$ and concentrated to give 125.1 mg of a mixture. $^1$H NMR of the crude shows 50% conversion yielding a 10:1 mixture of 30 to its diastereomer. Chromatography (40 g SiO$_2$, 6% EtOAc/94% CH$_2$Cl$_2$) gave 42.8 mg of starting material (34.5%), 43.0 mg of epoxy alcohol 30 (33%), and 3.0 mg of the minor epoxy alcohol. Spectral properties of 30: $^1$H NMR (CDCl$_3$, 360.134 MHz) δ:3.62 (1H, br), 3.58 (1H,m) 3.46 (1H,dJ=10.189 Hz), 2.57 (1H,d,J=9.51 Hz), 1.62 (1H,m), 1.5–1.3 (3H,m), 1.40 (3H,s), 1.30–1.15 (1H,m), 1.08 (3H,d,J=7.04 Hz), 0.94 (9H,t,J=7.91 Hz), 0.90 (3H,t,J=7.00 Hz), and 0.61 (6H,q,J=7.91 Hz). $^{13}$C NMR (CDCl$_3$, 90.55 MHz) δ:75.8, 66.6, 64.5, 61.9, 39.8, 35.3, 20.5, 19.7 15.5, 14.2, 6.8 and 6.7. IR (thin film): 3451 (br), 2960(s), 2877(s), 1458(s), 1379(s), 1240(s), 1149(s), 1096(s), 1006(s), 892(m), 843(m), 782(m), and 730(s) cm$^{-1}$. [α]D= +29.1° (c=2.28, CH$_2$Cl$_2$).

Example 25

(2S,3S,4S,5R)-5-(Triethylsilyloxy)-3-hydroxy-2,4-dimethyloctanal (31):

(2R,3S,4S,5R)-5-(Triethylsilyloxy)-2,3-epoxy-2,4-dimethyl-1-octanol (21.0 mg, 69.4 µmol) in 300 µl of THF at 0° C. was deprotonated with 1.05 eq of n-butyllithium. After 15 min, 0.1M samarium diiodide (764 µmol, 1.1 eq) was added and the reaction was allowed to warm to 25° C. over night. Then 1 ml of ½ saturated Rochelle's salt was added, stirred an additional 1 h, and poured onto 5 ml of Et$_2$O and 1 ml of H$_2$O. The layers were separated, extracted with ether (3×5 ml), washed with 5% NaHCO$_3$ (2×1 ml), brine (1×1 ml), dried over MgSO$_4$ and concentrated to give 31 crude.

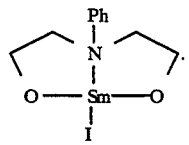

We claim:

1. A method for making an optically active compound of the formula (I)

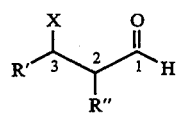

where X is a silyloxy group and R' and R" are independently selected from the group consisting of alkyl and aryl, comprising the steps of:
 (a) preparing an optically active epoxy alcohol of the formula (II)

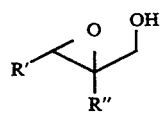

where R' and R" are as defined above; and (b) treating the epoxyalcohol with at least one reagent selected from the group consisting of (i) silyl triflates, and (ii) trialkylsilylhalides and Lewis acid.

2. A method as recited in claim 1, wherein the silyl triflate is a trialkylsilyl triflate.

3. A method as recited in claim 2, wherein the trialkylsilyl triflate is selected from the group consisting of t-butyldimethylsilyl triflate, triethylsilyl triflate, triisopropylsilyl triflate and trimethysilyl triflate.

4. A method as recited in claim 1, wherein the Lewis acid is BF$_3$.

5. A method for converting an aldehyde into an optically active compound of the formula (I)

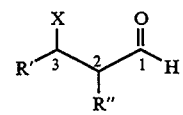

where X is a silyloxy group and R' and R" are independently selected from the group consisting of alkyl and aryl, comprising the steps of:
 (a) converting the aldehyde into an allylic alcohol using a Wittig reaction and reduction;
 (b) preparing an optically active epoxy alcohol by asymmetric epoxidation of the allylic alcohol; and
 (c) treating the epoxy alcohol with either
  (i) a silyl triflate, or
  (ii) a trialkylsilyl halide and a Lewis acid.

6. A method as recited in claim 5, wherein the silyl triflate is selected from the group consisting of t-butyldimethylsilyl triflate, triethylsilyl triflate, triisopropylsilyl triflate, and trimethysilyl triflate.

7. A method for making an optically active compound of the formula (Ia)

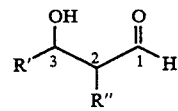

where R' and R" are independently selected from the group consisting of alkyl and aryl, comprising the steps of:
 (a) preparing an optically active epoxy alcohol of the formula (II)

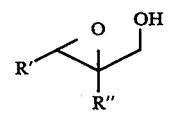

where R' and R" are as defined above;

(b) preparing a 3-silyloxyalkanal of the formula (I)

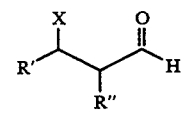

where X is a silyloxy group and R' and R" are as defined above, by treating the epoxy alcohol with at least one reagent selected from the group consisting of (i) silyl triflates and (ii) trialkylsilyl halides and Lewis acid; and (c) removing the 3-silyloxy group and replacing it with OH, by treating the 3-silyloxyalkanal with a deprotecting agent.

8. A method as recited in claim 7, wherein the deprotecting agent comprises hydrogen fluoride-pyridine complex.

9. A method as recited in claim 7, wherein the deprotecting agent comprises tetrabutylammonium fluoride.

10. A method for making an optically active 2-methyl-3-silyloxyhexanal, comprising the steps of:
(a) preparing an allylic alcohol;
(b) preparing an optically active epoxyalcohol by asymmetric epoxidation of the allylic alcohol using a chiral catalyst; and
(c) treating the epoxy alcohol with either
(i) a silyl triflate, or
(ii) a trialkylsilyl halide and a Lewis acid.

11. A method as recited in claim 10, wherein the silyloxyhexanal comprises a (2S,3R)-2-methyl-3-silyloxyhexanal, the allylic alcohol comprises an E-allylic alcohol, and the chiral catalyst comprises D-(−)diisopropyl tartrate.

12. A method as recited in claim 10, wherein the silyloxyhexanal comprises a (2R,3S)-2-methyl-3-silyloxyhexanal, the allylic alcohol comprises an E-allylic alcohol, and the chiral catalyst comprises L-(+)-diisopropyl tartrate.

13. A method as recited in claim 10, wherein the silyloxyhexanal comprises a (2S,3S)-2-methyl-3-silyloxyhexanal, the allylic alcohol comprises a Z-allylic alcohol, and the chiral catalyst comprises D-(−)-diisopropyl tartrate.

14. A method as recited in claim 10, wherein the silyloxyhexanal comprises a (2R,3R)-2-methyl-3-silyloxyhexanal, the allylic alcohol comprises a Z-allylic alcohol, and the chiral catalyst comprises L-(+)-diisopropyl tartrate.

15. A method as recited in claim 10, wherein the silyloxyhexanal is a 2-methyl-3-(trialkylsilyloxy)alkanal.

16. A method for making an optically active 1,3-diol, comprising the steps of
(a) preparing an optically active 2-silyloxyalkanal;
(b) reducing the aldehyde on the 2-silyloxyalkanal; and
(c) removing the silyloxy group and replacing it with OH.

17. A method for making a chiral polypropionate, comprising the steps of:
(a) preparing a chiral silyloxy epoxy alcohol; and
(b) treating the alcohol with
(i) an alkyl lithium or aryl lithium compound, and
(ii) a rare earth catalyst.

18. A method as recited in claim 17, wherein the rare earth catalyst comprises samarium diiodide.

19. A method as recited in claim 17, wherein the rare earth catalyst comprises a samarium compound having the formula